United States Patent [19]

Carr

[11] Patent Number: 4,609,759
[45] Date of Patent: Sep. 2, 1986

[54] PROCESS FOR PREPARING AMINO-2, 4-DINITROAROMATIC HERBICIDES

[75] Inventor: Richard V. C. Carr, Allentown, Pa.

[73] Assignee: Air Products and Chemicals, Inc., Allentown, Pa.

[21] Appl. No.: 606,323

[22] Filed: May 2, 1984

[51] Int. Cl.$^4$ ............................................. C07C 85/02
[52] U.S. Cl. ..................................... 564/395; 564/87; 564/406; 564/419; 544/167; 546/232; 548/569; 558/424
[58] Field of Search ................. 564/395, 406, 87, 419; 260/465 E; 544/167; 546/232; 548/569

[56] References Cited

U.S. PATENT DOCUMENTS

| | | | |
|---|---|---|---|
| 3,920,742 | 11/1975 | Lutz et al. | 260/577 |
| 4,025,538 | 5/1977 | Lutz et al. | 260/397.6 |
| 4,091,096 | 5/1978 | Beck et al. | 424/229 |
| 4,101,582 | 7/1978 | Lutz et al. | 260/57 X |
| 4,124,639 | 11/1978 | Lutz et al. | 260/573 |
| 4,165,231 | 8/1979 | Lutz et al. | 71/121 |

OTHER PUBLICATIONS

Houben–Weyl, "Methoden der Organischen Chemie", vol. XI/1, (Amines), Verlag, Stuttgart (1957), pp. 236–241.

Primary Examiner—Charles F. Warren
Assistant Examiner—John A. Sopp
Attorney, Agent, or Firm—Russell L. Brewer; E. Eugene Innis; James C. Simmons

[57] ABSTRACT

This invention pertains to a process for producing 2,6 dinitroaniline derivates which are suited as intermediates for herbicides. The process involves the formation of a 1,2,6-trinitro-aromatic isomer and the subsequent nucleophilic displacement of the 1-nitrosubstituent with an amine. The reaction products can easily be separated from other organics by forming an amine salt and extracting with water.

11 Claims, No Drawings

PROCESS FOR PREPARING AMINO-2, 4-DINITROAROMATIC HERBICIDES

TECHNICAL FIELD

This invention pertains to the synthesis of a variety of herbicides particularly the 2,6-dinitro-xylidine herbicides.

BACKGROUND OF THE INVENTION

A variety of substituted 2,6-dinitroaromatic compositions have been found to be extremely effective as pre-emergence herbicidal compositions. Many have been effective for controlling crab grass, pigweed, lambs quarters, wild oats, green foxtail, morning-glory and barnyard grass. Typically these compositions are prepared by chlorinating a substituted aromatic, then dinitrating the chlorinated 2,6-aromatic and displacing the labile chlorine atom with a primary or secondary amine to form the 2,6-dinitroaniline derivative. Representative compositions having pre-emergence herbicidal properties and methods for producing these compositions are shown in the following patents:

U.S. Pat. No. 3,920,742 discloses the preparation of N-sec-alkyl-2,6-dinitro-3,4 xylidine herbicide represented by the formula

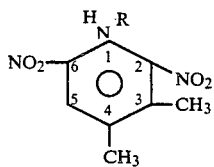

where R represents 1-ethylbutyl; 1-ethylpropyl; 1-methylpropyl, and 1-methylbutyl. The compositions are prepared by reacting the 1-chloro-2,6-dinitroaromatic, with an appropriately substituted primary or secondary amine at temperatures of from 50°–150° C. The compositions then are formulated into dust, dust concentrates, wettable powders, granulars, etc. for application to the soil that rates of about ⅛th to 20 pounds per acre of active material.

U.S. Pat. No. 4,025,538 discloses the preparation of 2,6-dinitroaniline compositions represented by the formula

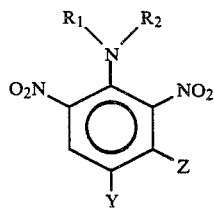

wherein

Y represents halogen, alkyl $C_1$–$C_4$, alkenyl $C_2$–$C_4$, $CF_3$, CN or —$SO_2NR_3R_4$;

Z represents alkyl $C_1$–$C_4$; alkenyl $C_2$–$C_4$ or mono-substituted alkyl $C_1$–$C_4$ where the substituent is halogen, $C_1$–$C_4$ alkoxy or —$NR_3R_4$;

$R_1$ represents hydrogen, $C_1$–$C_6$ alkyl, $C_2$–$C_6$ alkenyl or alkynyl $C_2$–$C_6$;

$R^2$ represents alkyl $C_{1-7}$ (straight, branched or cyclic), alkenyl $C_{2-6}$, alkynyl $C_{2-6}$, or mono-substituted alkyl $C_{1-4}$ where the substituent is halogen or alkyl $C_{1-4}$; and $R_3$ and $R_4$ each represent hydrogen or $C_1$–$C_4$ alkyl and where $R_1$ and $R_2$ when taken together represent piperidino, pyrrolidino, or morpholino.

These compositions are prepared by reacting an appropriately substituted amine with the halogenated derivative.

U.S. Pat. No. 4,091,096 discloses a variety of dinitroanilines for the control of phytopathogens, such compositions being represented by the formula

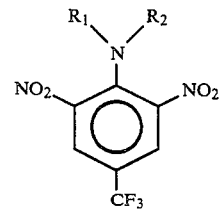

where $R_1$ is hydrogen, $C_2$–$C_3$ alkyl, chloroethyl, cyanoethyl, $C_3$–$C_4$ alkenyl or halo, $C_3$–$C_4$ alkenyl; and when $R_1$ is H, $R_2$ is $N(R_3)_2$ $C_3$–$C_6$ alkyl, branched $C_4$–$C_7$ alkyl containing no tertiary carbon atoms, 1-hydroxy-2-propyl, methallyl, N-ethyl-3-piperidyl, 2,6-dimethyl-1 piperidyl and the like. These compositions like the others are prepared by the nucleophilic substitution of a halogen atom in the 1-position by an amine.

U.S. Pat. Nos. 4,101,582; 4,124,639 and 4,165,231 show further variations in terms of composition and the methods of preparing 2,6-dinitroaniline herbicides. A variety of substituents are shown on these particular compositions.

SUMMARY OF THE INVENTION

This invention is based upon the finding that a 1,2,6-trinitro substituted aromatic compound of the formula

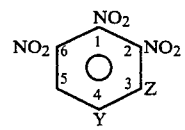

wherein

Y represents halogen, alkyl $C_1$–$C_4$, alkenyl $C_2$–$C_4$, $CF_3$, CN or —$SO_2NR_3R_4$;

Z represents alkyl $C_1$–$C_4$; alkenyl $C_2$–$C_4$ or mono-substituted alkyl $C_1$–$C_4$ where the substituent is halogen, hydroxyl $C_1$–$C_4$ alkoxy or —$NR_3R_4$;

$R_3$ and $R_4$ each represent hydrogen or $C_1$–$C_4$ alkyl; can be reacted with a primary or secondary amine of the formula $NHR_1R_2$ where $R_1$ and $R_2$ represents hydrogen, a $C_{1-6}$ alkyl, a $C_{2-6}$, alkenyl or $C_{2-6}$ alkynyl or when $R_1$ and $R_2$ taken together represent piperidino, pyrrolidino, or morpholino, to produce the 2,6-dinitro aniline type compositions which have utility as a pre-emergence herbicide.

This discovery permits one to synthesize the 2,6-dinitroaniline compositions by carrying out essentially two reactions, namely (1) trinitration of the aromatic composition and (2) the nucleophilic displacement of the 1-nitro radical in the aromatic composition with an amine.

Other advantages associated with the practice of this invention include:

an ability to produce a 2,6-dinitroaniline type composition in high selectivity;

an ability to form the 2,6-dinitroaniline type composition without intermediate purification of the reaction products; and an ability to obtain relatively purified product by simple separation techniques.

DETAILED DESCRIPTION OF THE INVENTION

For reference purposes the compositions that can be prepared by the practice of this invention and which have utility as pre-emergence herbicides for control of a variety of annual grasses and broadleaf weeds are represented by the formula

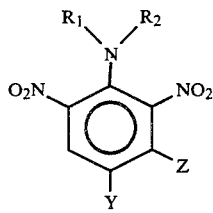

wherein

Y represents halogen, alkyl $C_1$–$C_4$, alkenyl $C_2$–$C_4$, $CF_3$, CN or —$SO_2NR_3R_4$;

Z represents alkyl $C_1$–$C_4$; alkenyl $C_2$–$C_4$ or monosubstituted alkyl $C_1$–$C_4$ where the substituent is halogen hydroxyl $C_1$–$C_4$ alkoxy or —$NR_3R_4$;

$R_1$ represents hydrogen, $C_1$–$C_6$ alkyl, $C_2$–$C_6$ alkenyl or alkynyl $C_2$–$C_6$;

$R^2$ represents alkyl $C_{1-7}$ (straight, branched or cyclic), alkenyl $C_{2-6}$, alkynyl $C_{2-6}$, or monosubstituted alkyl $C_{1-4}$ where the substituent is halogen or alkyl $C_{1-4}$ or $R_1$ and $R_2$ are combined together representing piperdino, pyrrolidino, or morpholino; and $R_3$ and $R_4$ each represent hydrogen or $C_1$–$C_4$ alkyl and where $R_1$ and $R_2$ when taken together represent piperidino, pyrrolidino, or morpholino.

Typically, the compositions are the 2,6-dinitro-N-alkyl 1,2-xylidines as described in U.S. Pat. Nos. 3,920,742; 4,101,582 and 4,025,538 which are hereby incorporated by reference.

To summarize the prior art, the general technique for forming the composition involved a three part synthesis; namely, the synthesis of a chlorobenzene intermediate by (1) reacting an appropriately substituted aniline with ethylchloroformate to yield the N-(ethoxycarbonyl) 3,4-substituted aniline; (2) dinitrating the corresponding N-(ethoxycarbonyl) 3,4-substituted aniline to form the N-(ethoxycarbonyl)-3,4-disubstituted-2,6-dinitroaniline and; (3) decomposing the N-ethoxycarbonyl product to the 3,4-disubstituted 2,6-dinitroaniline This invention is based upon a discovery that the 1,2,6-trinitroaromatic compositions, including substituted forms, will permit nucleophilic substitution of the 1-nitrosubstituent by an amine to produce the 2,6-dinitro-1-amino aromatic compositions which are suited as pre-emergence herbicides. As a result of this finding, the synthesis of the compositions is made much easier than in the prior art and eliminates numerous purification steps enroute to the finished product.

The process of the invention involves dinitrating an appropriately substituted aromatic compound of the formula

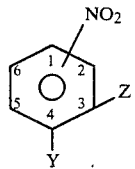

wherein

Y represents halogen, alkyl $C_1$–$C_4$, alkenyl $C_2$–$C_4$, $CF_3$, CN or —$SO_2NR_3R_4$; and Z represents alkyl $C_1$–$C_4$; alkenyl $C_2$–$C_4$ or monosubstituted alkyl $C_1$–$C_4$ where the substituent is halogen hydroxyl $C_1$–$C_4$ alkoxy or —$NR_3R_4$; to form a reaction product containing the 1,2,6-trinitroaromatic composition. Naturally, in any nitration of this type, the reaction mixture will comprise a mixture of isomers, typically the 1,2,6 and the 1,4,6 isomers. The advantage is that even though the 1,4,6 isomer is produced and is a trinitroaromatic composition, the 1-nitro group is not labile and therefore it does not undergo nucleophilic substitution on addition of reactive amine at the 1-position or at any other position. As a consequence, the 1,4,6-trinitroaromatic composition remains unchanged upon reaction with the amine and can be easily separated from the reaction product due to its water insolubility.

The nitration of the aromatic composition to produce the trinitroaromatic composition is well known and can be performed by conventional techniques e.g. the mixed acid technique as shown in U.S. Pat. No. 4,124,639. That subject matter is incorporated by reference. The mixed acid technique utilizes a mixture of nitric acid and sulfuric acid with the concentration of nitric acid typically being from 70 to 95 (fuming nitric acid) and the concentration of sulfuric acid being from 95 to 105 e.g., fuming sulfuric acid. Trinitration can be carried out in a continuous or batch mode at temperatures of from 30° to 80° C. and pressures of from atmospheres to 40 atmospheres psig. At the conclusion of the trinitration reaction, which generally is from 4 to 10 hours for the alkyl-substituted trinitroaromatic compounds, the aqueous phase is separated from the organic phase. The organic phase then is washed with water to remove residual traces of acid.

The conversion of the 1,2,6-trinitroaromatic composition to the 2,6 aromatic amine-1 is effected by reacting a primary or secondary amine with the labile nitro group on the 1,2,6-trinitroaromatic composition under conditions similar to those used in the nucleophilic substitution of the amine for a halogen atom as shown in U.S. Pat. No. 4,124,639. Representative amines have the formula $NHR_1R_2$ where $R_1$ and $R_2$ represent hydrogen, a $C_{1-6}$ alkyl, a $C_{2-6}$, alkenyl or $C_{2-6}$ alkynyl or are combined together to represent piperidino, pyrrolidino or morpholine. Specific amines include dibutylamine, butylamine, ethylpropylamine di-n-propylamine, propylamine, pentamine, allylamine, morpholine, piperidine and the like.

Typically the reaction is carried out dissolving the mixture of trinitroaromatic isomer composition in an inert solvent and then contacting the mixture with an appropriately substituted alkyl or alkenyl secondary amine. Temperatures are from 30° to 80° C. and pressures of from atmosphere to 20 atmospheres generally are utilized to effect reaction. Examples of inert solvent used for the nucleophilic substitution of the 1-nitro group on the aromatic composition include benzene, toluene, xylene, and the chlorinated solvents, such as, methylenechloride, chloroform, trichloroethylene and the like.

The 1, 2, 6 trinitro aromatic isomer will react with the secondary amine to produce the 2,6-dinitro-1-aniline derivative. This product then can be separated from the reaction mixture by converting the amine derivative to a water soluble amine salt e.g., by contacting the reaction product with concentrated sulfuric. The salt then dissolves in the aqueous phase and can be separated from the unreacted organic phase. The 1,2,4 trinitro isomer does not react with the amine and therefore remains water insoluble. Accordingly, a simple process separation scheme can be used.

The following examples are provided illustrate various embodiments of the invention.

EXAMPLE 1

Preparation of Trinitro-o-xylene

A 10.6 g sample (0.10 moles) of o-xylene was added dropwise into a vessel containing a solution of 14 g of 90 wt% nitric acid and 50 g of 97% sulfuric acid over a period of 12 minutes. The temperature rose from room temperature to 50° C. during this time and was held there an additional 3 minutes to effect reaction. After the reaction subsided, the phases were separated and the organic phase (largely a mixture of dinitro-o-xylenes) was recovered. This organic phase then was added to a vessel containing a solution of 100 g of 102% sulfuric acid and 14 g of 98.7% nitric acid at 70° C. over a period of five minutes. The temperature rose to 80° C. and the reaction, under moderate agitation, was maintained at that temperature for an additional 35 minutes. The reaction mixture was poured onto 200 g of ice and cooled. Crystals formed and were collected and dried. About 13.8 g of product comprising mixture of the 1,2,6 and 1,4,6 trinitro-o-xylene isomers were obtained as an off-white solid, the percent by weight of the 1,2,6 isomer was about 47%.

EXAMPLE 2

Preparation of 1-n-butyl-2,6-dinitro-o-xylene, 4

A 7.2 g portion of the reaction mixture from Example 1 was dissolved in 30 ml of methylene chloride. Then a 4.0 g sample of n-butyl amine was added to this mixture and the temperature rose from room temperature to 40° C. over a period of about three minutes. During this time the color of the reaction mixture turned from dark green to red. After reaction was complete, about 1 hour, the reaction mixture was contacted with two 40 ml aliquots of 90% $H_2SO_4$. The combined aqueous acid extracts were separated from the organic phase and poured onto 200 g of ice. A red-orange solid was collected and air dried yielding 3.11 g of 1,N-n-butyl-2,6-dinitro-3,4-xylidine. The melting point of the solid was 69° C.

The organic raffinate obtained after aqueous acid extraction above was washed with a 20 ml aliquot of water and then evaporated to yield 3.81 g of 1,4,6-trinitro-o-xylene as a pale yellow solid.

Example 2 shows that direct trinitration of o-xylene to form a mixture of the the isomeric trinitro-o-xylenes followed by reaction with an alkylamine avoids the necessity of obtaining a costly, isomerically pure 1-chloro, 2,6-dinitro-o-xylene starting material. Because only the 1-nitro group of 1,2,6-trinitro-o-xylene in the 1,2,6-trinitro-o-xylene/1,4,6-trinitro-o-xylene mixture is labile to nucleophilic aromatic substitution, treatment of the mixture yields only 2,6-dinitro 1-alkyl aniline derivative. As shown this composition can be readily converted to the amine salt and easily separated from the water insoluble 1,4,6-trinitro-o-xylene isomer.

EXAMPLE 3

The procedure of Example 2 was repeated except that a mixture of 1,2,6-trinitro-o-cresol was substituted for the 1,2,6-trinitro-o-xylene/1,4,6 trinitro-o-xylene isomer mixture. In this step 2.0 g (8.12 mmoles) of 1,2,6-trinitro-o-cresol was dissolved in 20 ml of methylene chloride. To this mixtue was added 1.4 g (22.96 mmoles) of isobutylamine. The solution immediately turned from yellow to red-orange and was then extracted once with 10 ml of 5% sulfuric acid. The organic phase was dried over sodium sulfate and evaporated to yield 2.08 g (97.6% yield) of orange-red crystals having a melting point of 97°–98° C.

To summarize it has been shown that a dinitro alkyl aniline herbide product may be obtained in two steps from o-xylene followed by a separation step which yields only the dinitro alkyl substituted aniline and a commercially valuable by-product, i.e., 1,4,6-trinitro-o-xylene. The nucleophilic aromatic substitution step of the process described herein is much more facile (i.e., approximately two orders of magnitude) than the counterpart step than the technique of effecting nucleophilic substitution of a chlorine atom.

The fact that the amine functionality in this process is incorporated after the nitration step rather than prior to nitration as in the scheme of the prior art also precludes formation of N-nitro-1 and N-nitroso-1 by-products which must be removed from the dinitro alkyl substituted aniline prior to effecting subsequent chemical reactions. Otherwise valuable organic intermediates would have been lost.

What is claimed is:

1. In a process for the preparation of 2,6-dinitroaniline compositions represented by the formula

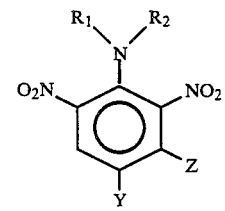

wherein
Y represents halogen, alkyl $C_1$–$C_4$, alkenyl $C_2$–$C_4$, $CF_3$, CN or —$SO_2NR_3R_4$;
Z represents alkyl $C_1$–$C_4$; alkenyl $C_2$–$C_4$ or mono-substituted alkyl $C_1$–$C_4$ where the substituent is halogen, hydroxyl $C_1$–$C_4$ alkoxy or —$NR_3R_4$;
$R_1$ represents hydrogen, $C_1$–$C_6$ alkyl, $C_2$–$C_6$ alkenyl or alkynyl $C_2$–$C_6$;
$R^2$ represents alkyl $C_{1-7}$ (straight branched or cyclic), alkenyl $C_{2-6}$, alkynyl $C_{2-6}$, or mono-substituted alkyl $C_{1-4}$ where the substituent is halogen or alkyl $C_{1-4}$ or combined with $R_1$ to represent piperidino, pyrrolidino, or morpholino; and
$R_3$ and $R_4$ each rerpresent hydrogen or $C_1$–$C_4$ alkyl and where $R_1$ and $R_2$ when taken together represent piperidino, pyrrolidino, or morpholino, wherein a 2,6-dinitroaromatic compound having a labile group in the 1 position is reacted with a primary or secondary amine represented by the formula NHR₁R₂, with R₁ and R₂ being defined as above, the improvement comprising utilizing a 2,6-dinitro aromatic compound having a labile nitro group in the 1-position as said 2,6-dinitroaromatic compound.

2. The process of claim 1 wherein Y is methyl or CF³.

3. The process of claim 2 wherein Z in said formula is hydroxy or alkyl $C_{1-4}$.

4. The process of claim 3 wherein R₂ is alkyl $C_{1-4}$.

5. The procss of claim 4 wherein R₁ is alkyl $C_{1-4}$.

6. The process of claim 5 wherein both Y and Z are methyl.

7. In a process for forming the composition represented by the formula

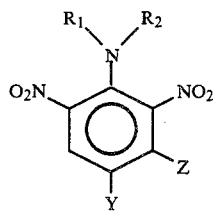

wherein

Y represents halogen, alkyl $C_1-C_4$, alkenyl $C_2-C_4$, CF₃, CN or —SO₂NR₃R₄;

Z represents alkyl $C_1-C_4$; alkenyl $C_2-C_4$ or monosubstituted alkyl $C_1-C_4$ where the substituent is halogen, hydroxyl $C_1-C_4$ alkoxy or —NR₃R₄;

R₁ represents hydrogen, $C_1-C_6$ alkyl, $C_2-C_6$ alkenyl or alkynyl $C_2-C_6$;

R² represents alkyl $C_{1-7}$ (straight branched or cycle), alkenyl $C_{2-6}$, alkynyl $C_{2-6}$, or monosubstituted alkyl $C_{1-4}$ where the substituent is halogen or alkyl $C_{1-4}$ or is combined with R₁ to form piperidino, pyrrolidino, or morpholino; and R₃ and R₄ each represent hydrogen or $C_1-C_4$ alkyl and where R₁ and R₂ when taken together represent piperidino, pyrrolidino, or morpholino, the improvement which comprises:

dinitrating a composition represented by the formula

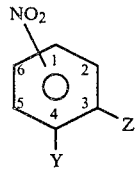

wherein Y represents halogen, alkyl $C_1-C_4$, alkenyl $C_2-C_4$, CF₃, OH CN or —SO₂NR₃R₄; and Z represents alkyl $C_1-C_4$; alkenyl $C_2-C_4$ or monosubstituted alkyl $C_1-C_4$ where the substituent is halogen, hydroxyl $C_1-C_4$ alkoxy or —NR₃R₄; by the mixed phase technique utilizing nitric acid and sulfuric acid to produce a 1,2,6-trinitro aromatic composition; and reacting said 1,2,6-trinitro aromatic composition with a primary or secondary amino represented by the formula NHR₁R₂ where R₁ and R₂ represents hydrogen, a $C_{1-6}$ alkyl, a $C_{2-6}$, alkeny or $C_{2-6}$ alkynyl or R₁ and R₂ are combined together to form piperidino, pyrrolidino, or morpholino;

converting said 2,6-dintroaniline composition to an amine salt;

separating the thus formed water soluble amine salt from the organic phase; and then neutralizing the salt to form the amine.

8. The process of claim 7 wherein Y and Z are methyl groups.

9. The process of claim 8 wherein R₁ and R₂ are $C_{1-4}$ alkyl groups.

10. The process of claim 7 wherein said composition which is nitrated is o-xylene and the resulted trinitro o-xylene is reacted with n-butylamine.

11. The process of claim 7 wherein Y is a CF₃.

* * * * *